US008551333B2

(12) United States Patent
Lin et al.

(10) Patent No.: US 8,551,333 B2
(45) Date of Patent: Oct. 8, 2013

(54) PARTICLE-BASED MICROFLUIDIC DEVICE FOR PROVIDING HIGH MAGNETIC FIELD GRADIENTS

(75) Inventors: Adam Yuh Lin, Irvine, CA (US); Tak Sing Wong, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 500 days.

(21) Appl. No.: 12/594,179

(22) PCT Filed: Apr. 7, 2008

(86) PCT No.: PCT/US2008/004483
§ 371 (c)(1), (2), (4) Date: Sep. 30, 2009

(87) PCT Pub. No.: WO2009/008925
PCT Pub. Date: Jan. 15, 2009

(65) Prior Publication Data

US 2010/0044232 A1 Feb. 25, 2010

Related U.S. Application Data

(60) Provisional application No. 60/907,501, filed on Apr. 5, 2007.

(51) Int. Cl.
*B03C 1/02* (2006.01)
*C12M 1/00* (2006.01)

(52) U.S. Cl.
USPC ................... 210/222; 252/62.51 R; 422/68.1; 422/502; 422/504; 422/527; 435/287.2; 435/308.1; 436/526; 436/806

(58) Field of Classification Search
USPC ........... 210/222; 252/62.51 R; 422/68.1, 502, 422/504, 527; 435/287.2, 308.1; 436/526, 436/806
See application file for complete search history.

(56) References Cited

U.S. PATENT DOCUMENTS

2004/0018611 A1 1/2004 Ward et al.
2008/0124779 A1* 5/2008 Oh et al. .................... 435/173.9

FOREIGN PATENT DOCUMENTS

WO WO 2009008925 A2 * 1/2009

OTHER PUBLICATIONS

Written Opinion of the International Searching Authority for PCT/US08/04483, dated Nov. 29, 2008.*
Chalmers; et al., "Flow Through, Immunomagnetic Cell Separation", Biotechnol. Prog. (1998), 14(1):141-148.

(Continued)

*Primary Examiner* — David A Reifsnyder
(74) *Attorney, Agent, or Firm* — Bozicevic, Field & Francis LLP; Pamela J. Sherwood

(57) ABSTRACT

A microfluidic device for manipulating particles in a fluid has a device body that defines a main channel therein, in which the main channel has an inlet and an outlet. The device body further defines a particulate diverting channel therein, the particulate diverting channel being in fluid connection with the main channel between the inlet and the outlet of the main channel and having a particulate outlet. The microfluidic device also has a plurality of microparticles arranged proximate or in the main channel between the inlet of the main channel and the fluid connection of the particulate diverting channel to the main channel. The plurality of microparticles each comprises a material in a composition thereof having a magnetic susceptibility suitable to cause concentration of magnetic field lines of an applied magnetic field while in operation. A microfluidic particle-manipulation system has a microfluidic particle-manipulation device and a magnet disposed proximate the microfluidic particle-manipulation device.

12 Claims, 9 Drawing Sheets

(56) References Cited

OTHER PUBLICATIONS

Chalmers; et al., "Theoretical Analysis of Cell Separation Based on Cell Surface Marker Density", Biotechnology and Bioengineering (1998), 59(1)10-20.
Choi; et al., "Development and Characterization of Microfluidic Devices and Systems for Magnetic Bead-Based Biochemical Detection", Biomedical Microdevices (2001), 3(3):191-200.
Dudley, "To Bead or Not to Bead", Journal of Immunotherapy (2003), 26(3):187-189.
Gijs, "Magnetic bead handling on-chip: new opportunities for analytical applications", Microfluid Nanofluid (2004), 1:22-40.
Han; et al., "Paramagnetic capture mode magnetophoretic microseparator for high efficiency blood cell separations", Lap Chip (2006), 6:265-273.
Hoyos; et al., "Study of magnetic particles pulse-injected into an annular SPLITT-like channel inside a quadrupole magnetic field", Journal of Chromatography (2000), 903:99-116.
Hu; et al., "Marker-specific sorting of rare cells using dielectrophoresis", PNAS (2005), 102(44):15757-15761.
Inglis; et al., "Continuous microfluidic immunomagnetic cell separation", Applied Physics Letter (2004), 85 (21):5093-95.
Krupke; et al., "Separation of Metallic from Semiconducting Single-Walled Carbon Nanotubes", Science (2003), 301:344-347.
Miwa; et al., "Development of micro immunoreaction-based cell sorter for regenerative medicine", The First International Conference on Bio-Nano-Information Fusion, Jul. 20-22, 2005, 4 pages.
Ramadan; et al., "An integrated microfluidic platform for magnetic microbeads separation and confinement", Biosensors and Bioelectronics (2006), 21:1693-1702.
Ramadan; et al., "Magnetic-based microfluidic platform for biomolecular separation", Biomed Microdevices (2006), 8:151-158.
Reddy; et al., "Determination of the Magnetic Susceptibility of Labeled Particles by Video Imaging", Chemical Engineering Science (1996), 51(6):947-956.
Sun; et al., "Continuous, Flow-Through Immunomagnetic Cell Sorting in a Quadrupole Field", Cytometry (1998), 33:469-475.
Suzuki; et al., "A Chaotic Mixer of Magnetic Bead-Based Micro Cell Sorter", Journal of MIcroelectromechanical Systems (2004), 13(5):779-790.
Xia; et al., "Combined microfluidic-micromagnetic separation of living cells in continuous flow" Biomed Microdevices (2006), 8:299-308.
Zborowski; et al., "Analytical Magnetapheresis of Ferritin-Labeled Lymphocytes", Analytical Chemistry (1995), 67 (20):3702-3712.

* cited by examiner

| Image Set \ Trial | Ni | Magnet | Cell |
|---|---|---|---|
| 1 | 8.88E-03 | 2.03E-03 | 6.43E-04 |
| 2 | 7.29E-03 | 3.41E-03 | 2.67E-04 |
| 3 | 8.46E-03 | 3.18E-03 | 6.54E-05 |
| 4 | 8.31E-03 | 1.76E-03 | 2.26E-03 |
| 5 | 8.10E-03 | 2.54E-03 | 8.87E-04 |
| 6 | 7.96E-03 | 3.94E-03 | 2.27E-03 |
| 7 | 7.71E-03 | 3.10E-03 | -6.89E-04 |
| 8 | 7.67E-03 | 2.86E-03 | 1.58E-04 |
| 9 | 8.01E-03 | 3.39E-03 | 2.33E-03 |
| 10 | 7.94E-03 | 1.36E-03 | 6.50E-04 |
| 11 | 7.73E-03 | 2.60E-03 | 2.55E-03 |
| 12 | 8.40E-03 | 3.41E-03 | 6.35E-04 |
| 13 | 8.36E-03 | 3.44E-04 | 1.99E-03 |
| 14 | 8.19E-03 | 1.20E-03 | 7.08E-04 |
| 15 | 8.12E-03 | 1.47E-03 | 7.17E-04 |

| | | | |
|---|---|---|---|
| Average | 8.08E-03 | 2.44E-03 | 1.03E-03 |
| Standard Error | 1.01E-04 | 2.66E-04 | 2.57E-04 |
| Standard Deviation | 3.89E-04 | 1.03E-03 | 9.95E-04 |
| Variance | 1.52E-07 | 1.07E-06 | 9.89E-07 |
| Stand Err/Avg % | 1.2 | 10.9 | 25.0 |

| | Ni - Magnet | Magnet - Cell | Ni - Cell |
|---|---|---|---|
| t-value | 19.79 | 3.81 | 25.55 |

Figure 7A

| | | Ni | Mag | Ni/Mag |
|---|---|---|---|---|
| **Experimental** | **First Order Coeff.** | 8.08E-03 | 2.44E-03 | 3.31 |
| **Simulation** | $\Delta B^2/\Delta x$ | 2.79E-07 | 1.06E-07 | 2.64 |

PARTICLE-BASED MICROFLUIDIC DEVICE FOR PROVIDING HIGH MAGNETIC FIELD GRADIENTS

CROSS-REFERENCE TO RELATED APPLICATION

The application is a 371 National Phase Application of PCT/US08/04483 filed Apr. 7, 2008, which claims priority to U.S. Provisional Application No. 60/907,501 filed Apr. 5, 2007, the entire contents of which are hereby incorporated by reference.

This invention was made with Government support under Grant No. DK070328 awarded by the National Institutes of Health and Grant No. NCC2-1364 awarded by NASA. The Government has certain rights in this invention.

BACKGROUND

1. Field of Invention

This application relates to microfluidic devices, and more particularly microfluidic devices that can be used to generate high magnetic field gradients in microfluidic channels.

2. Discussion of Related Art

The contents of all references, including articles, published patent applications and patents referred to anywhere in this specification are hereby incorporated by reference.

Many cell or bio-particle separation or concentration techniques require large electric or magnetic field gradients, such as dielectrophoresis (see, e.g., R. Krupke, F. Hennrich, H. von Lohneysen and M. M. Kappes, *Science,* 2003, 301(5631), 344-347). Unlike macro-scale devices, high magnetic field gradients in Micro Total Analysis Systems (μTAS) are difficult to generate. Previous developments to generate large magnetic field gradients were achieved by changing the shape and position of magnets that surrounded main fluidic channels. Quadrupole and dipole magnetic systems had been successful for separating cells in channels with diameters in the millimeter range (L. P. Sun, M. Zborowiski, L. R. Moore, and J. J. Chalmers, *Cytometry,* 1998, 33.4, 469-475; M. Hoyos, L. R. Moore, K. E. McCloskey, S. Margel, M. Zuberi, J. J. Chlamers and M. Zborowski, *Journal of Chromatography,* 2000, 903, 99-116). The purity of the separated sample is high (99%) but the recovery rate, defined as the percent of target cells recovered from the original sample, is unstable (37-86%) (J. J. Chalmers, M. Zborowski, L. P. Sun and L. Moore, *Biotechnology Progress,* 1998, 14.1, 141-148). Recent developments use MEMS technology to generate magnetic field gradients through the use of micro-coils and magnetic pillars (Q. Ramadan, V. Samper, D. P. Poenar and C. Yu, *Biosensors & bioelectronics,* 2006, 21.9, 1693-1702; Q. Ramadan, V. Samper, D. P. Poenar and C. Yu, *Biomedical microdevices,* 2006, 8.2, 151-158). Although these platforms can easily manipulate the magnetic beads in batches, they do not provide a continuous separation.

The above-mentioned, conventional MEMS magnetic devices require non-trivial and expensive multi-layer fabrication processes in order to integrate the magnetic materials with the microfluidic channels to achieve magnetic-particle separation. Therefore, there is a need for microfluidic devices and systems that have a structure that permits ease of fabrication while still achieving magnetic-based separation.

SUMMARY

A microfluidic device for manipulating particles in a fluid according to an embodiment of the current invention has a device body that defines a main channel therein, in which the main channel has an inlet and an outlet. The device body further defines a particulate diverting channel therein, the particulate diverting channel being in fluid connection with the main channel between the inlet and the outlet of the main channel and having a particulate outlet. The microfluidic device also has a plurality of microparticles arranged proximate or in the main channel between the inlet of the main channel and the fluid connection of the particulate diverting channel to the main channel. The plurality of microparticles each comprises a material in a composition thereof having a magnetic susceptibility suitable to cause concentration of magnetic field lines of an applied magnetic field while in operation.

A microfluidic particle-manipulation system according to an embodiment of the current invention has a microfluidic particle-manipulation device and a magnet disposed proximate the microfluidic particle-manipulation device.

BRIEF DESCRIPTION OF THE DRAWINGS

The invention is better understood by reading the following detailed description with reference to the accompanying figures in which:

FIG. 1A is a mask layout for the microfluidic device. B was the inlet for the sample. A, C, and D were inlets for media. E was the outlet of the waste sample and F was the outlet for separated sample. G was the inlet for the nickel particles. H was the outlet for nickel particles. The G-H channel was the adjacent nickel channels for enhanced magnetic field gradient generation.

FIG. 7A is a table of the first order coefficients from line fitting in MATLAB for all three trials. The coefficients equal $V_y/V_x$. The cell trial is the control experiment. The t-values are presented at the bottom of the table.

DETAILED DESCRIPTION

Figures 1A, 1B:
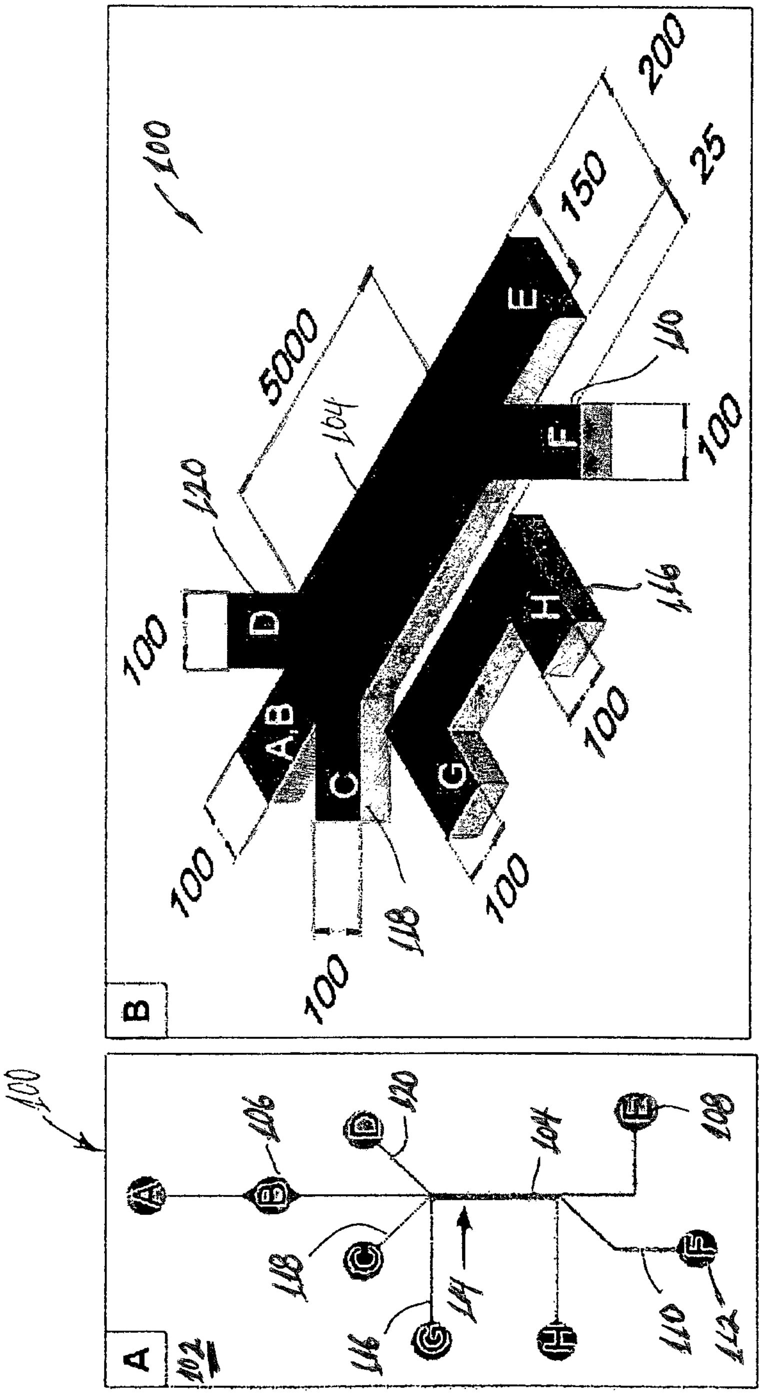
FIGS. 1A, B, and C are schematic illustrations of a microfluidic device according to an embodiment of the current invention.
FIG. 1B is a schematic illustration showing the corresponding channel dimensions, unit in μm.
Figure 1C:
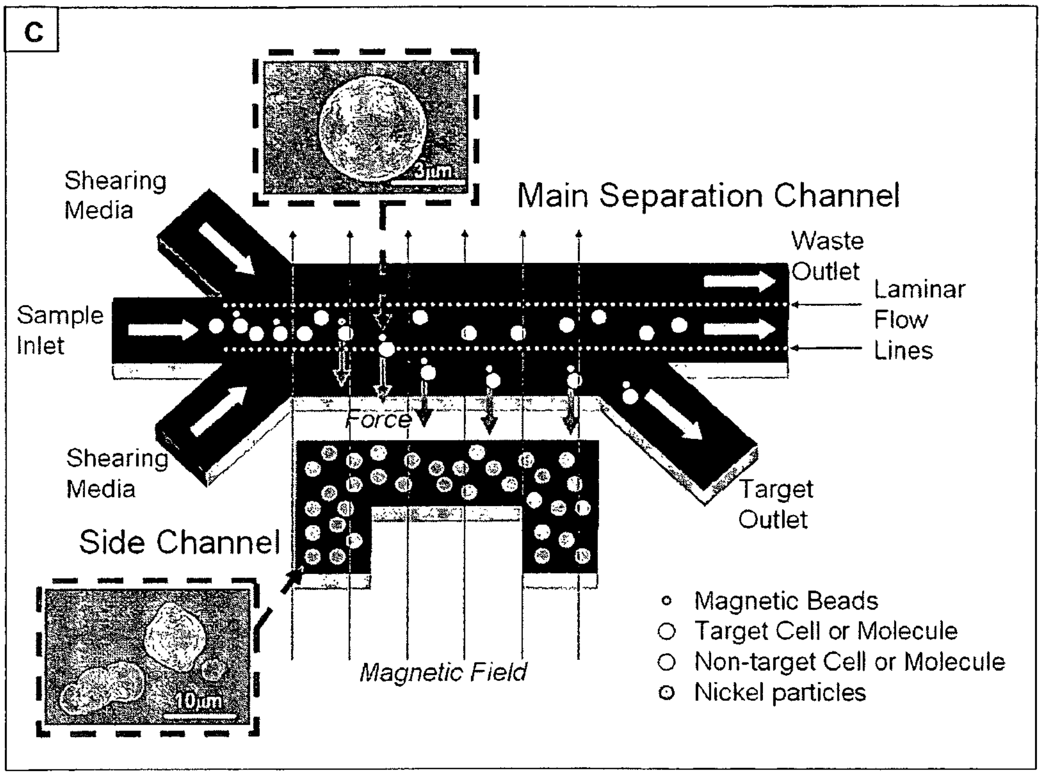
FIG. 1C is a schematic illustration showing the concept of separation of cells/particles attached to magnetic beads using metal (nickel) particles as media to generate large magnetic field gradients according to an embodiment of the current invention.

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

Some embodiments of the current invention can provide magnetic MEMS fluidic devices that can perform cell separation and that can be produced by simple single-layer, single-mask fabrication techniques. Generally, magnetic cell separation or manipulation requires a carrier such as a magnetic bead to attach to the target cells. Some available magnetic beads, also known as DYNABEADS (INVITROGEN, CA), are 4.5 μm superparamagnetic cores with polystyrene shells. The surfaces of the beads can be coated with antibodies targeted towards specific cell membrane markers for certain cell types. Methods for handling the magnetic beads have been very crucial for biochemical and analytical applications (M. A. M. Gijs, *Microfluidcs and nanofluidics,* 2004, 1, 22-40; J. W. Choi, K. W. Oh, A. Han, C. A. Wijayawardhana, C. Lannes, S. Bhansali, K. T. Schlueter, W. R. Heineman, H. B. Halsall, J. H. Nevin, A. J. Helmicki, H. T. Henderson and C. H. Ahn, *Biomedical microdevices,* 2001, 3.3, 191-200). A large interest in cell separation within automated systems has grown among the medical field especially for oncology or hematology research.

Figures 2A, 2B, 2C, 2D:
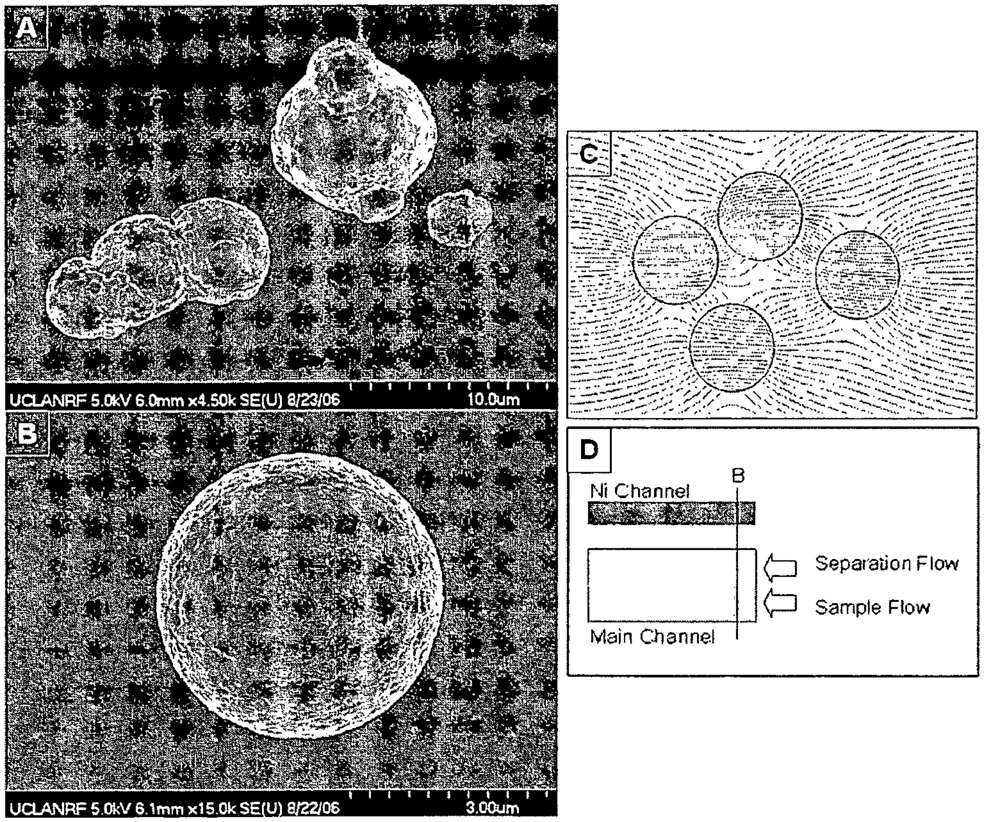
FIG. 2A shows a scanning electron microscope (SEM) picture of nickel microparticles that are suitable for use with some embodiments of the current invention.
FIG. 2B shows a SEM picture of magnetic beads that are suitable for use with some embodiments of the current invention.
FIG. 2C shows results for a simplified one-dimensional magnetostatic computer simulation for Ni microparticles bending a uniform magnetic field using a simplified one-dimensional magnetostatic model with commercial software (COMSOL Multiphysics).
FIG. 2D is a schematic illustration to facilitate the explanation of some concepts of the current invention. The arrows are the direction of fluid flow.

FIG. 1A is a schematic illustration of a microfluidic device 100 for manipulation of particles in a fluid according to an embodiment of the current invention. The microfluidic device 100 has a device body 102 that defines a main channel 104. (FIG. 1B is a schematic illustration showing an enlarged view of the channel structure of FIG. 1A.) The main channel 104 has an inlet 106 and an outlet 108. The device body 102 further defines a particulate diverting channel 110. The particulate diverting channel 110 is in fluid connection with the main channel 104 between the inlet 106 and the outlet 108 of the main channel 104 and has a particulate outlet 112. A plurality of microparticles 114 are arranged proximate the main channel 104 between the inlet 106 of the main channel 104 and the fluid connection point of the particulate diverting channel 110 to the main channel 104. (See also FIGS. 2A, 2C and 2E for examples of possible pluralities of microparticles 114 in an embodiment of the current invention.) For example, the plurality of microparticles 114 may be mixed with a fluid and injected into a side channel 116 that is arranged proximate the main channel 104. The plurality of microparticles 114 each includes a material that has a magnetic susceptibility suitable to cause concentration of magnetic field lines of an applied magnetic field while the microfluidic device 100 is in operation. The microfluidic device 100 can be connected to other microfluidic devices and can also have additional structures in various embodiments of the current invention. For example, the microfluidic device 100 may include hydrodynamic focusing channels 118 and 120. For channels that are constructed sufficiently small, such as the main channel, fluid traveling through the main channel will exhibit laminar flow. Fluid introduced into the hydrodynamic focusing channels 118 and 120 will force the fluid already flowing through the main channel 104 towards the center into a narrower sheath of fluid. The fluid in the channels can be a liquid in which particulate matter is dispersed. For example, there may be biological cells dispersed in the fluid. In addition, the particulate matter can have magnetic particles attached, such as magnetic particles attached to biological cells.

FIGS. 2A-2D help explain some of the concepts of some embodiments of the current invention. Small metal particles, such as nickel, are utilized as the media to concentrate magnetic fields. However, the general concepts of the current invention are not limited to only microparticles made from nickel. All the channels, for example the main channel 104, the diverting channel 110 and the side channel 116 can be monolithically fabricated in a single step according to some embodiments of the current invention. This can greatly simplify methods of manufacturing microfluidic devices according to some embodiments of the current invention. The presence of the nickel particles in an adjacent side channel increases the magnitude of the magnetic field density gradient which corresponds to an increase in the force exerted on the magnetic beads. Apart from the ease of device fabrication according to some embodiments of the current invention, stable and high recovery rates due to sophisticated force control within the microenvironment can be achieved in some embodiments. In addition, the fabrication cost for the device can be relatively low, which can lead to mass production and commercialization for clinical or research purposes.

Theory

The magnetic force generated on a magnetic bead is governed by the following equation (M. Zborowski, C. B. Fuh, R. Green, L. P. Sun, and J. J. Chalmers, *Analytical chemistry,* 1995, 67.20, 3702-3712):

$$F_b = \frac{1}{2\mu_0}\Delta\chi \cdot V_b \cdot \nabla B^2 \tag{1}$$

where $\mu_0$ is the magnetic permeability of free space; $\Delta\chi$ is the difference of susceptibility between the magnetic bead and the surrounding medium; $V_b$ is the volume of the bead; and B is the magnetic field density. It is important to recognize that a gradient of magnetic field density is required for a translational force. A strong uniform magnetic field can only cause rotational force, but not translational force.

The total force acting on a cell with magnetic beads attached is:

$$F_m = A_c \cdot \alpha \cdot \beta \cdot F_b \tag{2}$$

where $A_c$ is the total surface area of the cell, $\alpha$ is the number of target cell surface markers per membrane surface area, $\beta$ is the number of antibodies bound per marker, and the $F_m$ is the force acting on one magnetic bead.

Countering the magnetic force is the drag force defined by the Stokes drag law:

$$F_d = 6\pi \cdot \eta \cdot r \cdot v \tag{3}$$

where $\eta$ is the viscosity of the medium; r is the radius of the cell; and v is the velocity of the cell moving through the medium.

Assuming that gravity and buoyant forces are negligible, the two forces combine into:

$$F_m + F_d = ma \tag{4}$$

where m is the mass of the cell and a is the acceleration of the cell. The inertial term ($\sim 10^{-11}$) is several orders smaller than the total magnetic force and the Stokes drag force ($\sim 10^{-6}$) (S. Reddy, L. R. Moore, L. Sun, M. Zborowski and J. J. Chalmers, *Chemical engineering science,* 1996, 51.6, 947-956). Thus, we can neglect the inertial term in the equation (4). This assumption allows us to find the relationship between the lateral velocity that provides distinct separation and the minimum magnetic field density gradient ($\nabla B^2$) required.

Plugging in equations (1), (2), and (3) into equation (4), the relation between the magnetic field gradient and the velocity of the cell moving in media is obtained:

$$\nabla B^2 = \frac{12\pi \cdot \mu_0 \cdot \eta \cdot r}{A_c \cdot \alpha \cdot \beta \cdot \Delta\chi \cdot V_b} v \tag{5}$$

By attempting to calculate the relationship between $\nabla B^2$ and v, the following assumptions were made. First, the number of magnetic beads bound to each surface marker ($\beta$) is assumed to be a constant, which, in this case, equals 1. Second, we assume that the number of markers per area of cell surface ($\alpha$) is also a constant. If one bead is bound to each cell, $\alpha$ equals $8.84 \times 10^9$ beads/$M^2$ (J. J. Chalmers, M. Zborowski, L. Moore, S. Mandal, B. B. Fang, and L. Sun, *Biotechnology and bioengineering,* 1998, 59.1, 10-20). Third, the susceptibility of the media ($\sim 10^{-6}$) is negligible compared to the susceptibility of magnetic beads (0.245). Fourth, the diameter of the cell is between 3 μm to 10 μm. We assume the diameter of the cell is 6 μm. Other constants are permeability of free space, $\mu_0 = 4\pi \times 10^{-7}$ $Hm^{-1}$, and the viscosity of media, $\eta = \sim 10^{-3}$ $Nsm^{-1}$. By measuring the velocity ratio, we will be able to find the ratio of the total magnetic force on the cell/bead complex.

Examples

Material and Methods

Channel Fabrication

Different channel geometries were designed in conventional computer-aided design software and printed out onto a negative transparency mask (PHOTOPLOT, CO). The channels were fabricated using replicate molding techniques. The mold was fabricated using SU-8 negative photoresist (MICROCHEM, MA) on a silicon wafer. The thickness of the mold was ~50 μm. Then, a polydimethylsiloxane mixture (PDMS), at a composition of 1 to 10 (weight ratio of curing agent to PDMS), was poured onto the mold and subsequently cured at 60° C. for 4 hours. After the curing process, the PDMS replicate was peeled off and punched with inlets and outlets at designated locations. To complete the fabrication procedures, both the PDMS channel surface and a glass substrate were activated by oxygen plasma in order to bond the two surfaces together (see FIGS. 1A and 1B).

All inlets and outlets are 100 μm in width with the exception of outlet E, which is 150 μm. The main channel is 200 μm in width while the adjacent channel has a 100 μm width. The two channels are 25 μm apart. In addition, a 500 μL syringe was used at inlet C while 250 μL syringes were applied for the rest of the inlet locations (A, B, and D). A sample, which was a mixture of cells and magnetic beads, entered the device from inlet B. Cell growth media was inserted from inlets A, C, and D. Inlet A was designed to serve the purpose of pushing stagnated cells and beads that were stuck in inlet B into the main channel. Media from inlets C and D constitute two streams of sheath flows that focus the sample flow into a fine central stream through hydrodynamic focusing. This microfluidic focusing technique allowed us to adjust the position and the width of the sample stream in the same channel design.

System Setup

Figure 3:
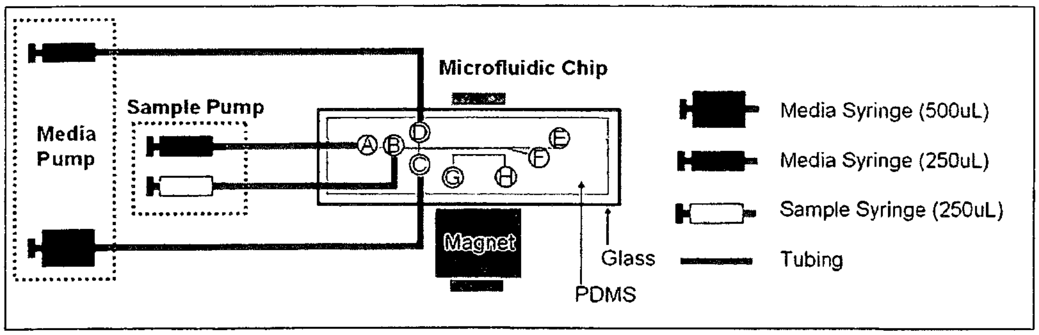
FIG. 3 A schematic illustration showing system connections according to an embodiment of the current invention. The syringes for inlet A and B were placed on one syringe pump (sample pump) and the other two (C, D) syringes were placed on another syringe pump (media pump). The top small magnet was used in holding the bottom magnet in place.

Following the DYNABEAD protocol from INVITROGEN, 25 μL of magnetic beads were added to 1 mL of B-lymphocyte sample (Coriell Institute, NJ), at a cell density of approximately $10^6$ cells/mL and mixed for 30 minutes in a 1.5 mL microcentrifuge tube. Magnetic beads that are commonly found for analytical purposes are 4.5 μm in diameter and made from polystyrene superparamagnetic material (M. E. Dudley, *Journal of immunotherapy,* 2003, 26.3, 187-189). The B-lymphocytes were cultured in RPMI 1640 (MEDIATECH, VA) with 10% FBS and antibiotics 1×PSN (SIGMA-ALDRICH, MO). The cells were stained by an addition of 0.5 μL of MITOTRACKER red dye (INVITROGEN, CA). The dye was excited by green light and fluoresced red light. Roughly 20% volume ratio of glycerol was added to the sample tube to prevent the precipitation of cell/beads complexes in the syringe during the experiment (X. Hu, P. H. Bessette, J. Qian, C. D. Meinhart, P. S. Daugherty, and H. T. Soh, *Proceedings of the National Academy of Sciences of the United States of America,* 2005, 102.44, 15757-15761). 100 μL of prepared mix sample was put in a 250 μL gas-tight glass syringe (Hamilton, Nev.) and connected to inlet B. Then growth media was filled into two 250 μL syringes (connected to inlets A and D) and a 500 μL syringe (connected to inlet C) (FIG. 3). Once the setup was completed, the syringes were connected to the microfluidic chip with soft tubing. (The microfluidic chip in this example is an example of a microfluidic device 100 according to an embodiment of the current invention.) The chip was placed on an inverted microscope (NIKON TE2000U) that was connected to a CCD camera (AG HEINZE, CA). All the fluid media were pumped through digitally controlled syringe pumps (HARVARD APPARATUS, MA). The fluid pumping speed for the sample syringe (inlet B), along with one of the 250 μL media syringe (inlet A) was set at 0.2 μL/min, while the other 250 μL media syringe (inlet D) and the 500 μL media syringe (inlet C) was set at 1 μL/min.

In order to demonstrate the functioning of the increased magnetic field gradient in the presence of nickel particles, three different conditions were tested: (1) in the absence of magnet and nickel particles (termed as Cell trial), (2) in the presence of a magnet but without nickel particles (termed as Magnet trial), and (3) with the presence of both magnet and nickel particles (termed as Ni trial). The Cell trial was the control experiment that served as a reference to compare with the later results. Comparison of the Magnet trial and the Ni trial determined the contribution of the nickel particles to the magnetic field gradient generation. The magnet in the experiments used was a NdFeB cube magnet with a side length of 4.76 mm (3/16") (AMAZING MAGNETS, CA). In order to hold the magnet in place on one side of the chip, another small plate magnet was placed in the other side of the chip with the dimensions of3.18 mm×3.18 mm'1.59 mm (1/8"×1/8"×1/6"). For the Ni trial, the nickel particles, with less than 20 μm in diameter (Atlantic Equipment Engineers, NJ), were immersed in silicone oil that carried the particles into the adjacent side channel from inlet G. Fluorescence images were taken at four different locations of the main channel to quantitatively measure the locus of the cells that were subjected to external magnetic field. At each location, 15 pictures were taken with a 10 second exposure time. The pictures were used for further data analysis that will be explained in the next section.

Results

Simulation

Figures 4A, 4B, 4C, 4D, 4E:
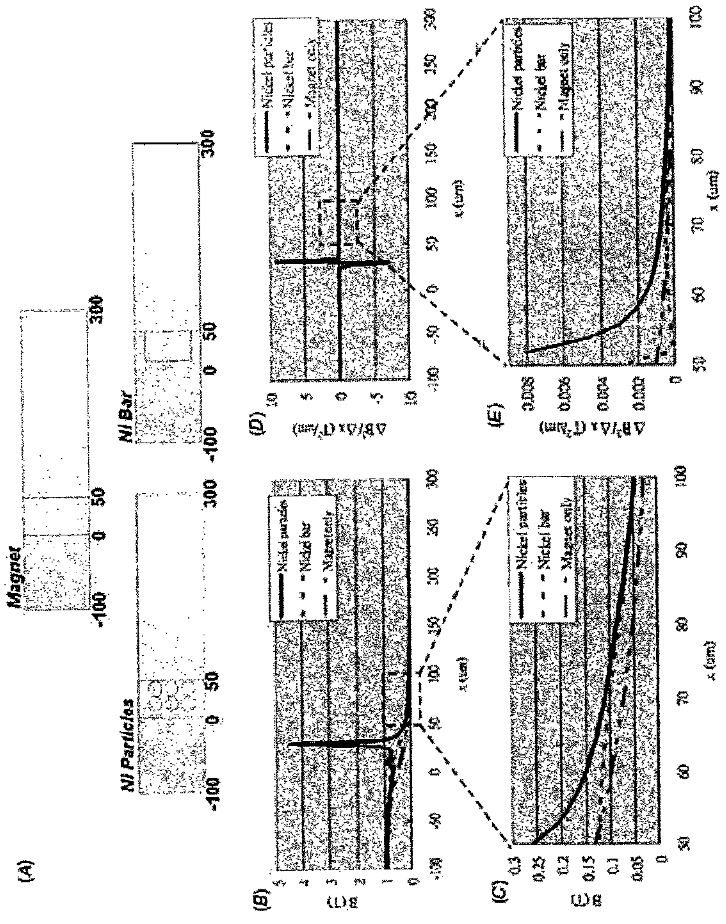
FIG. 4A is a simulation of the magnetic field density with Ni particles, Ni bar, and magnet only. The nickel particles and the nickel bar were placed in between 0 and 50 μm on the graphs.
FIG. 4B is a graph showing the magnetic field density across the center of each simulation case.
FIG. 4C is a magnified portion of FIG. 4B showing the magnetic field density of the center line from 50 to 100 μm.
FIG. 4D is the discrete one-dimensional gradient ($\Delta B^2/\Delta x$) for each simulation case.
FIG. 4E is a magnified portion of FIG. 4D showing the discrete one-dimensionlee$B^2/\Delta x$) between 50 to 100 μm.

To predict the performance of the resulting magnetic separation scheme in the presence of nickel particles as a magnetic field concentrator, simulations were carried out using a simplified one-dimensional magnetostatic model by commercial software (COMSOL Multiphysics). In the simulation, a 100 μm length square magnet with 1 T was positioned behind the origin. Simulations showed that the magnetic field decreased dramatically within 100 μm from the magnet and remained at the same intensity level afterwards (FIG. 4A). This showed that the maximum force can only be obtained near the magnet (i.e. within 100 μm from the magnet). To implement this physically, magnets need to be fabricated in extremely close proximity to the sample channel in order for this scheme to be effective for cell separation. This involved a multi-layered MEMS fabrication scheme which would be costly and it complicated the device fabrication, prohibiting mass production of the device.

In another scenario, nickel particles were put in between the magnet and the fluid to extend the effective range of the magnetic field, and the resulting effects were simulated. The presence of the nickel particles concentrates the magnetic field by bending the field lines. This concentration of the magnetic field would cause a local substantial magnetic field gradient to occur, resulting in enhanced magnetic force on the magnetic beads (FIG. 4B). From equation (1), the force is directly proportional to the gradient of the squared magnetic field density ($\nabla B^2$). The change of magnetic field density squared over the change of position (x) is shown in FIG. 4C. The ratio between the values of $^{\Delta}B^2/^{\Delta}x$ with nickel particles and without the particles showed that the addition of nickel particles is expected to create a force that is roughly 20 times larger than that with magnets only. This ratio converges to around three at 200 μm away from the edge of the magnet (FIG. 4D).

Data Analysis

Figures 5A, 5B:
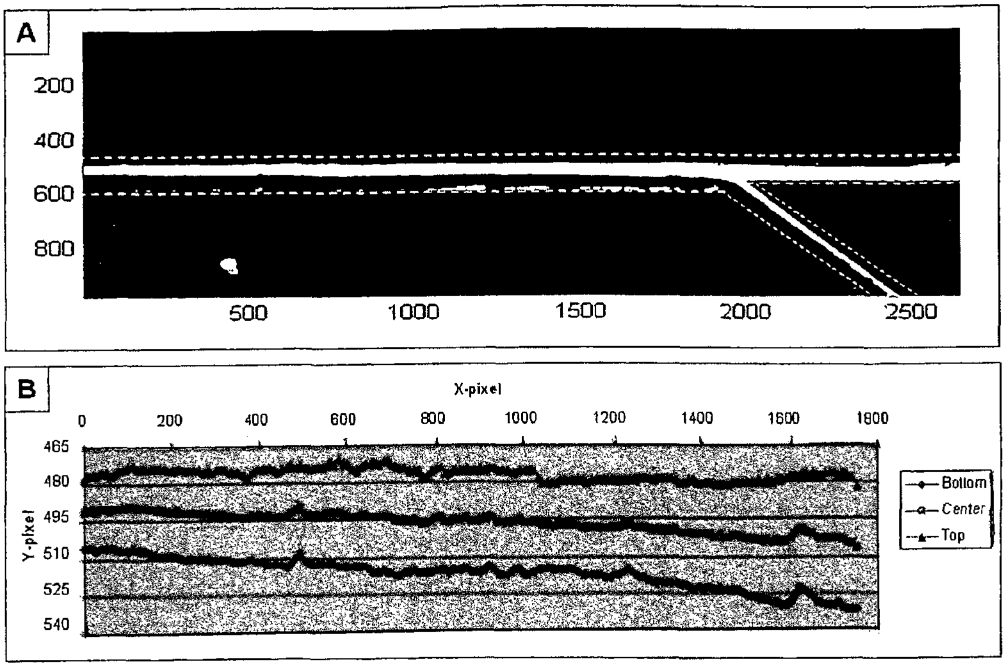
FIG. 5A shows the locus of the sample stream under the influence of the external magnetic field. The white particles on the bottom of the channel were cells that were pulled out of the stream. This only happened with the presence of nickel particles. The white dotted lines represent the edges of the main channel.
FIG. 5B shows the locus plot showing the locus of the upper, center and lower bound of the sample stream. In every 10 pixels, the upper and the lower bound of the white stream was taken and averaged. The average of the two created a centerline which was line fitted to obtain the first order coefficient.
Figure 6:
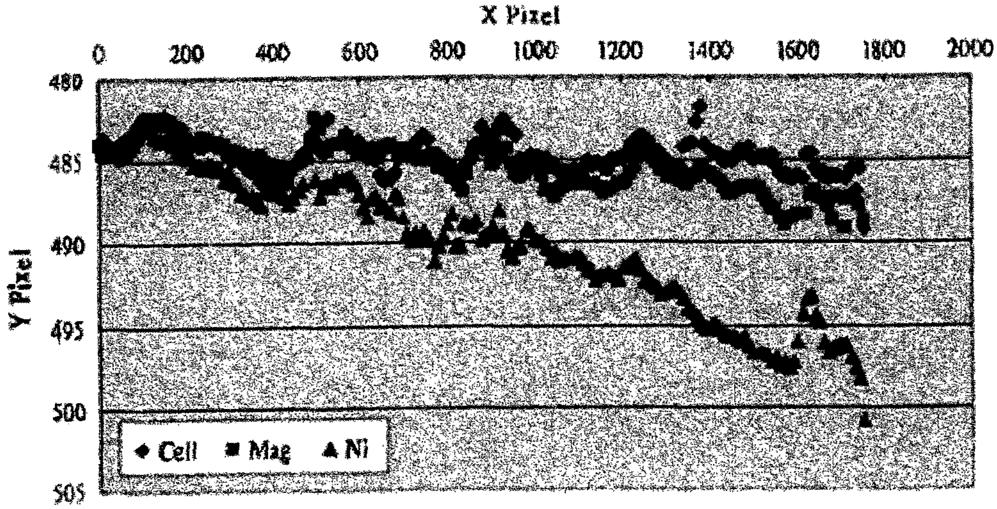
FIG. 6 shows one set of the center line data of cells from all three trials: Ni trial (with the presence of both magnet and nickel particles), Magnet trial (with the presence of magnet only), Cell trial (in the absence of magnet and nickel particles). The starting points were offset to the same starting y value for easier visual comparison.

Since the images were taken in 4 different locations of the main channel, in order to reconstitute the locus of the sample stream, the images were combined using pre-defined alignment points. The images from the first position did not have any usable alignment points; therefore, images from the other three positions were further analyzed. Pictures from each of the three positions were randomly chosen and linked together to become partial channel images. The images were further processed to enhance the signal-to-noise level for later data analysis purpose (FIGS. 5A and 5B). The locus of the sample stream was traced and drawn from the images. The bending of this locus was caused by the force pulling on the magnetic beads attached to the cells. From the center line data of all 15 pictures for the three different trials, the bending of the line from the Ni trial was significantly larger than the Magnet trial and the Cell trial (FIG. 6).

The velocity values were extracted from the image data to quantify the difference between the three trials. The horizontal velocity of the complex ($V_x$) is constant for each experiment since $V_x$ depends on the flow rate of the sample and the shear media. Considering $V_x$ as a constant, the time traveled equals the position (x) over the horizontal velocity ($V_x$). On the other hand, the vertical velocity ($V_y$) depends on the force exerted on the cell/bead complex. From equation (5), the total magnetic force is directly proportional to the velocity of the complex. Since the vertical y range is comparably small, the magnetic force within this range can be assumed to be constant. Therefore, according to equation (5), the velocity of the cell/bead complex should be constant. The bending of the locus would provide us with the vertical velocity ($V_y$), governed by the equation:

$$y = \frac{V_y}{V_x} \cdot x + y_0 \tag{6}$$

where t is the travel time of the cell/bead complex, $V_x$ and $V_y$ are exponents of velocity of the complex, and $y_0$ is the starting position of the sample stream. The ratio of the dimensionless first order coefficients in different trials can be used to quantify and compare the vertical velocity which can be translated into the magnetic forces exerted on the complexes.

Figures 7B, 7C:
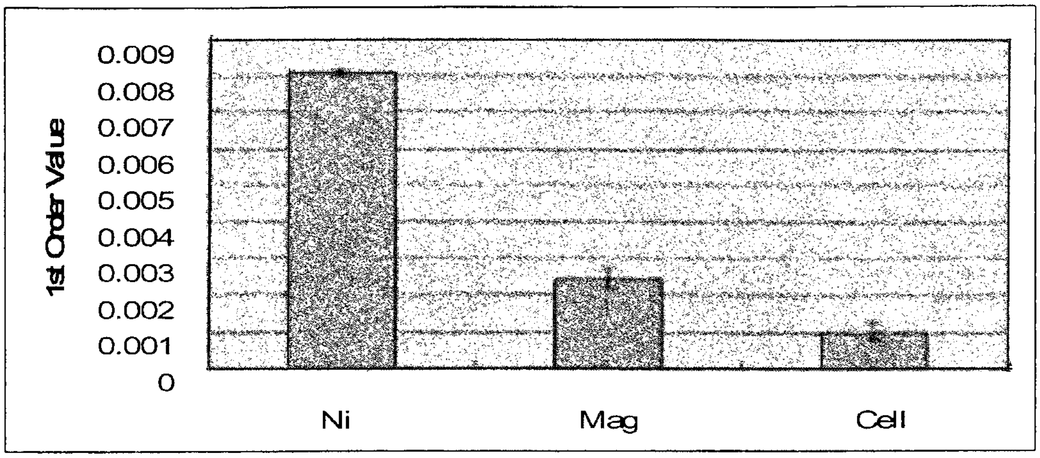
FIG. 7B shows the first order coefficient averages for all three trials. The Ni trial has a larger average than the Magnet and control Cell trial.
FIG. 7C is a table of the experimental ratio for second order coefficient compared with the Simulation data ratio for $^{\Delta}B^2/^{\Delta}x$. The simulation data ratio is assumed to be proportional to the induced magnetic force ratio from the coefficient data in different trials.

After running the data through a line fitting function (MATLAB), the average first order coefficient over the 15 sets of data for the Ni trial was $8.08\times10^{-3}$ with a standard error of $1.01\times10^{-4}$ while the average for the Magnet trial was $2.44\times10^{-3}$ with a standard error of $2.66\times10^{-4}$. The Cell trial (i.e. the control experiment) had an average of $1.03\times10^{-3}$ with a standard error of $2.57\times10^4$ (see the table in FIG. 7A). The percentage of standard error over the average was only 1.2% for the Ni trial, 10.9% for the Magnet trial, and 25.0% for the Cell trial (FIG. 7B). The ratio of the average Ni trial first order coefficient and the average magnet trial first order coefficient was 3.26 (see the table in FIG. 7C).

We performed a t-test to confirm the significance of our data. The t-value between the Ni trial and Magnet trial was 19.79. The t-value between the Magnet trial and Cell trial was 3.81. The t-value between the Ni trial and Magnet trial was 25.55. A t-value of 2.76 corresponded to a p-value of 0.01 for a two-tailed test. Therefore, the p-value for the Ni/Magnet trial and the Ni/Cell trial should be significantly lower then 0.001. Even though the t-value for the Magnet/Cell trial was larger than 2.76, the p-value would be closer to 0.01 than the other p-values since the t-values for the other two comparisons were 5 times greater. However, overall, the three trials were considered statistically different.

The experimental results in conjunction with the simulation results help demonstrate that the presence of small metal particles, such as nickel, in an adjacent channel according to an embodiment of the current invention was able to generate a large magnetic field gradient, translating into an enhanced magnetic force for cell/bead manipulation or separation. The average ratio of the first order coefficients in the Ni and Magnet trials showed that the induced magnetic force in the presence of nickel particles were more than three times stronger compared to the absence of the nickel particles. The averages were shown to be significantly different from the t-test. However, from the t-values, the statistical difference between the Magnet trial and the Cell trial was considerably smaller than difference between the Ni trial and the Magnet trial or the Cell trial. The p-value for Magnet/Cell trial was only slightly lower than 0.01. In addition, the percentage of standard error over the averages of the Magnet (11%) and Cell trials (25%) showed that the variations among the sample were greater than the averages from the Ni trial (1%). For the case of the Cell trial, the relatively large standard deviation was believed to originate from the random diffusion of the complexes or instability of the system such as disturbance from the tubing. Similar to the case of the Cell trial, the 11% standard error over average from the Ni trial showed that systems using pure magnets would have a great deal of variation. In comparison, the presence of nickel particles in an adjacent channel as a magnetic field concentrator has provided an enhanced force field for particle manipulation as well as maintaining a more stable and controllable system.

The experimental force ratio of the Ni trial/Magnetic trial was larger than the simulated results. From the fluorescent images, the measured distance between the sample stream and the adjacent channel is 151 μm. Since the borderline of the last nickel particle was at 50 μm in the simulation, the ratio of $^{\Delta}B2/^{\Delta}x$ of interest is at 201 μm. According to the simulation data, the ratio of $^{\Delta}B2/^{\Delta}x$ at 201 μm had the value of 2.64. (See the table in FIG. 7C.) The ratio of $^{\Delta}B2/^{\Delta}x$ can be assumed equivalent to the force ratio because the magnetic field density gradient is the dominant factor in the magnetic force equation. The experimentally determined force ratio of 3.31 was noticeably greater than the simulated result (i.e. force ratio=2.64), suggesting that more prominent effects can be achieved with closer separation between the sample and the adjacent channels (FIG. 4D).

Figure 8:
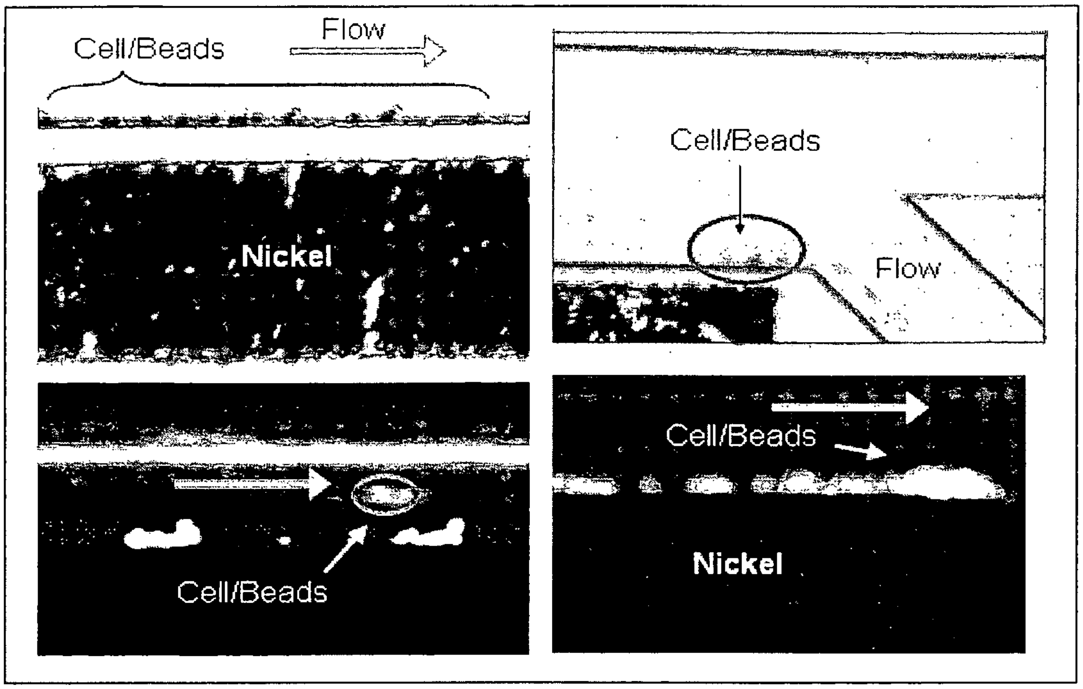
FIG. 8 shows that the cell/bead complexes stayed attached to the bottom of the channel and were trapped. The upper two pictures show the beads at the bottom of the channel. The bottom two pictures show cells with fluorescent markers at the bottom of the channel. The arrows indicate the flow direction. The bottom left circle shows a cell moving away from the main stream due to the induced force from the magnetic field gradient generated by the nickel particles.

Although this proof-of-concept prototype has proven the desired effects, a number of improvements can be done to maximize the performance of the device according to some embodiments of the current invention. Parameters such as the length and width of the main channel as well as the flow rates for the media and sample are important for dictating the resulting cell separation performance. The design and position of the adjacent nickel channel are important elements for improving the recovery rate for sample separation. Since the nickel particles are self aligned, different nickel density within the channel and different channel shape and design can offer different effects. Occasionally, some cell/bead complexes would be attracted towards the sidewall of the channel that was closed to the corner of the adjacent nickel channel. This phenomenon further supports that stronger magnetic force field can be generated with reduced separation distance between the channels (FIG. 8).

Some embodiments of the current invention have advantages over the conventional micro-magnetic cell separation devices, such as relatively low cost of production. Recent magnetic bead manipulation platforms require intensive MEMS fabrication technology which are economically expensive and time consuming (Q. Ramadan, V. Samper, D. P. Poenar and C. Yu, *Biosensors & bioelectronics,* 2006, 21.9, 1693-1702; K. H. Han, and A. B. Frazier, *Lab on a chip,* 2006, 6.2, 265-273; D. W. Inglis, R. Riehn, R. H. Austin, and J. C. Sturm, *Applied physics letters,* 2004, 85.21, 5093-5095; J. W. Choi, *Biomedical microdevices,* 2001, 3.3, 191-200; J. Miwa, W. H. Tan, Y. Suzukui, N. Kasagi, N. Shikazono, K. furukawa, and T. Ushida, *The First International Conference on Bio-Nano-Information Fusion*, Marina del Ray, Calif., 2005). Fabrication methods according to some embodiments of the current invention are replicate molding techniques which only require a single mask layer for the manufacturing process. However, general concepts of the current invention are not limited to only single-mask-layer fabrication. In addition, the mold can be reused multiple times to fabricate new channels for testing and optimizing the system.

Figure 9A:
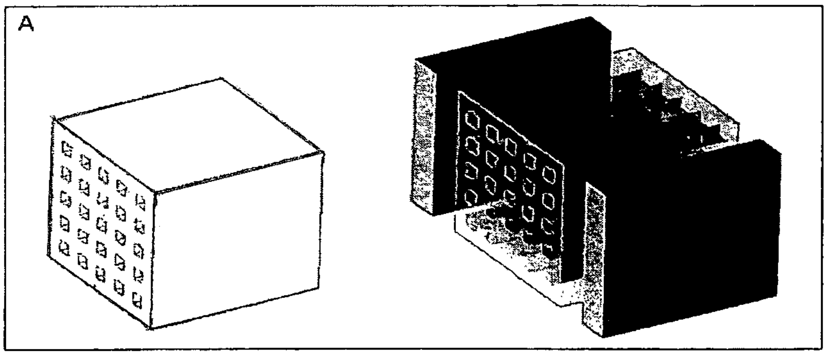
FIG. 9A is a schematic illustration of a cell separation cube, which is an example of a microfluidic block according to an embodiment of the current invention. The small squares stand for an optimized microfluidic device containing a main channel and an adjacent metal particle channel. The two rectangular boxes are magnets that provide a magnetic field across the cube. The sample flows through the small squares in the cube.

Upon optimizing channel designs for maximized cell separation recovery rate and purity, other embodiments of the current invention can include producing high-throughput microfluidic cell separation arrays. For example, other embodiments of microfluidic devices according to the current invention can be a microfluidic chip that has a plurality of structures such as those of the microfluidic device 100. This may be a planar array, for example, which could be produced as a single or multiple microfluidic chips. Another embodiment of the current invention may include, for example, an array of microfluidic channels fabricated in a plastic or acrylic cube to provide a microfluidic block (FIG. 9A). This cube-shaped cell separator (microfluidic block) can provide a large throughput while maintaining a well controlled microenvironment for separation. These cell separator arrays can be disposable due to their low manufacturing cost. In addition, multiple cell separation events can be performed in one single step upon the application of the magnetic field according to some embodiments of the current invention. The choices of the metal particles are relatively flexible, provided that their permeabilities are large enough for the device to be effective. An automated separation system according to some embodiments of the current invention can be further coupled with a microfluidic cell and magnetic bead mixer (H. Suzuki, C. M. Ho, N. Kasagi, *Journal of microelectromechanical systems,* 2004, 13.5, 779-790). Practitioners using a device according to this embodiment of the current invention are only required to provide suitable magnetic beads and place the sample in the specified container. The separation can then be done automatically. Such a system can be useful for researchers who want to study certain cell types or bio-particles from a tissue or blood sample.

Other aspects of the current invention can include cell trapping and cell/particle concentration in addition to cell/ particle separation, for example. Generally, it can provide a new device and methods for manipulating particles. It can also be integrated into devices for rare blood cell isolation, specific stem sell isolation and stimulated to fully differentiate at the outlet, DNA or other biomolecule concentration and detection, etc.

Furthermore, the channel design can be selected according to the specific application it is targeted toward. For example, once the geometry is optimized for high efficient magnetic bead-based cell separation, the device can be particularly helpful for hospitals and biology laboratories to replace differential centrifugation separation. Since the device can be made out of acrylic or other plastic blocks, it can be disposed of after every use. The entire cell separation system can be automated, reducing time for researchers or technicians. Other applications include using the magnetic force to trap individual cells for research purposes as well as designing the geometry for rare blood cell isolation or even cancer cell isolation.

The nickel can be replaced with other types of metal for the microparticles that have higher susceptibility, such as, but not limited to, iron. Iron is hard and currently costly to microfabricate with traditional methods, but it can be easily and economically used in some embodiments of this invention. Similar to magnetic fields, electric fields may also be bent or manipulated using different particles to create dielectrophoretic forces. Other side channel geometries can allow different applications such as single cell trapping, biomolecule detection or concentration, magnetic particle assembly, etc.

According to other embodiments of the current invention, metal particles can be introduced into one or multiple shear streams, such as the hydrodynamic focusing streams. Even though this may contaminate the sample and might be biologically incompatible in some applications, the particles in the shear streams could be a good method for applications that require a stronger magnetic force in some embodiments of the current invention.

Figure 9B:
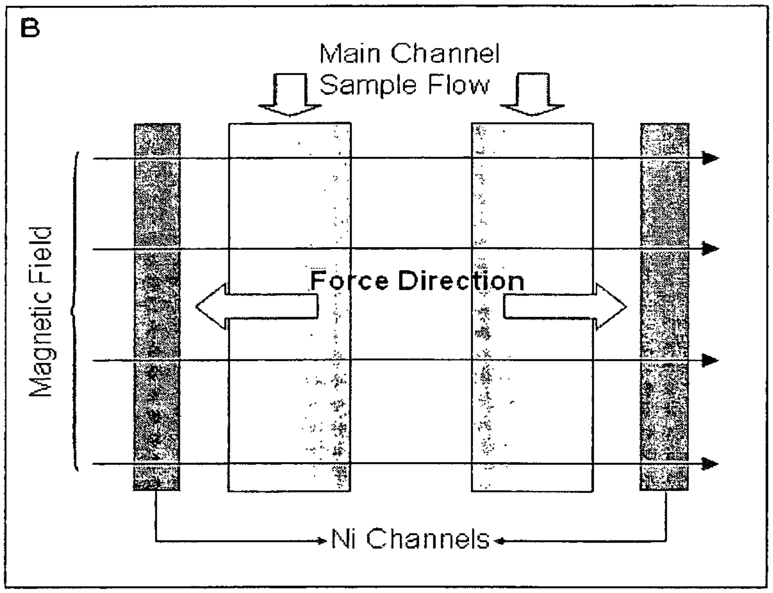
FIG. 9B is a schematic illustration of the microfluidic device of FIG. 9A inside the small squares. The force direction depends on the relative position between the main channel and the nickel or other metal particle channel, and does not depend on the direction of the magnetic field.

The throughput volume range for devices and systems according to some embodiments of the current invention can be very large. If small volume processes, such as for pediatric research, are required, a device according to an embodiment of the current invention could process a volume in the microliter range since the flow rate for the sample is less than 1 μL/min. Different small volumes can also be processed by changing the channel width and length. If large volume processes, such as blood screening, are required, the devices can be made in arrays to work parallel. The array can be made from a plastic cube such as acrylic, for example, and the separation channel and side channel can be fabricated with lasers according to one embodiment. The devices can be made on top of each other and can use only one external magnetic source in some embodiments of the current invention (see FIG. 9, for example).

The current invention is not limited to the specific embodiments of the invention illustrated herein by way of example, but is defined by the claims. One of ordinary skill in the art would recognize that various modifications and alternatives to the examples discussed herein are possible without departing from the scope and general concepts of this invention.

What is claimed is:

1. A microfluidic device for manipulation of particles in a fluid, comprising:

a device body defining a main channel therein, said main channel comprising an inlet and an outlet; said device body further defining a particulate diverting channel therein, said particulate diverting channel being in fluid connection with said main channel between said inlet and said outlet of said main channel and comprising a particulate outlet; said device body further defining a side channel therein, said side channel proximate and not connected to said main channel;

a fluid disposed within said side channel; and a plurality of microparticles dispersed in said fluid, wherein said plurality of microparticles each comprises a material in a composition thereof having a magnetic susceptibility suitable to cause concentration of magnetic field lines of an applied magnetic field while in operation.

2. A microfluidic device according to claim 1, wherein said plurality of microparticles comprise at least one of nickel and iron in a composition thereof.

3. A microfluidic device according to claim 1, wherein said device body is a microfluidic chip, said main channel and said diverting channel being arranged substantially along a common plane within said microfluidic chip.

4. A microfluidic device according to claim 3, further comprising a plurality of hydrodynamic focusing channels connected to said main channel defined by said microfluidic chip, wherein all of said hydrodynamic focusing channels are arranged substantially along a common plane within said microfluidic chip.

5. A microfluidic device according to claim 1, wherein said device body is a microfluidic chip, said main channel, said diverting channel and said side channel being arranged substantially along a common plane within said microfluidic chip.

6. A microfluidic device according to claim 1, wherein said device body is a microfluidic block.

7. A microfluidic particle-manipulation system, comprising:

a microfluidic particle-manipulation device; and a magnet disposed proximate said microfluidic particle-manipulation device, wherein said microfluidic particle-manipulation device comprises:

a device body defining a main channel therein, said main channel comprising an inlet and an outlet;

said device body further defining a particulate diverting channel therein, said particulate diverting channel being in fluid connection with said main channel between said inlet and said outlet of said main channel and comprising a particulate outlet; said device body further defining a side channel therein, said side channel proximate and not connected to said main channel;

a fluid disposed within said side channel; and a plurality of microparticles dispersed in said fluid, and wherein said plurality of microparticles each comprises a material in a composition thereof having a magnetic susceptibility suitable to cause concentration of magnetic field lines of an applied magnetic field while in operation.

8. A microfluidic system according to claim 7, wherein said plurality of microparticles comprise at least one of nickel and iron in a composition thereof.

9. A microfluidic system according to claim 7, wherein said device body is a microfluidic chip, said main channel and said diverting channel being arranged substantially along a common plane within said microfluidic chip.

10. A microfluidic system according to claim 7, wherein said device body is a microfluidic chip, said main channel, said diverting channel and said side channel being arranged substantially along a common plane within said microfluidic chip.

11. A microfluidic system according to claim 9, further comprising a plurality of hydrodynamic focusing channels connected to said main channel defined by said microfluidic chip, wherein all of said hydrodynamic focusing channels are arranged substantially along a common plane within said microfluidic chip.

12. A microfluidic system according to claim 7, wherein said device body is a microfluidic block.

* * * * *